US006830789B2

(12) United States Patent
Doane et al.

(10) Patent No.: US 6,830,789 B2
(45) Date of Patent: Dec. 14, 2004

(54) CHIRAL ADDITIVES FOR CHOLESTERIC DISPLAYS

(75) Inventors: Joseph W. Doane, Kent, OH (US); Asad A. Khan, Kent, OH (US); Alexander J. Seed, Stow, OH (US)

(73) Assignees: Kent Displays, Inc., Kent, OH (US); Kent State University, Kent, OH (US)

( * ) Notice: Subject to any disclaimer, the term of this patent is extended or adjusted under 35 U.S.C. 154(b) by 0 days.

(21) Appl. No.: 09/937,210

(22) PCT Filed: Jun. 8, 2001

(86) PCT No.: PCT/US01/14842

§ 371 (c)(1),
(2), (4) Date: Sep. 24, 2001

(87) PCT Pub. No.: WO01/96494

PCT Pub. Date: Dec. 20, 2001

(65) Prior Publication Data

US 2002/0187281 A1 Dec. 12, 2002

Related U.S. Application Data

(60) Provisional application No. 60/210,485, filed on Jun. 9, 2000.

(51) Int. Cl.[7] .................. C09K 19/52; C07D 317/12
(52) U.S. Cl. .................. 428/1.3; 252/299.01; 428/1.1; 549/430; 549/453
(58) Field of Search .................. 428/1.1; 252/299.01, 252/299.62, 299.7; 549/430, 453

(56) References Cited

U.S. PATENT DOCUMENTS

| 5,328,638 | A | * | 7/1994 | Muller et al. | 252/299.61 |
| 5,637,255 | A | * | 6/1997 | Kelly et al. | 252/299.61 |
| 5,651,918 | A | * | 7/1997 | Scherowsky et al. | 252/299.61 |
| 5,681,504 | A | * | 10/1997 | Buchecker et al. | 252/299.61 |
| 6,099,751 | A | * | 8/2000 | Meyer et al. | 252/299.61 |
| 6,495,217 | B2 | * | 12/2002 | Farrnd | 428/1.1 |

FOREIGN PATENT DOCUMENTS

WO        WO 02/06265        * 1/2002

OTHER PUBLICATIONS

CA 124:9076, 1996.*
Kuball et al., "TADDOLs with Unprecedent Helical Twisting Power in Liquid Crystals", Helv. Chim. ACTA, vol. 80, pp. 2507–2514, 1997.*

* cited by examiner

*Primary Examiner*—Shean C. Wu
(74) *Attorney, Agent, or Firm*—Pearne & Gordon LLP

(57) ABSTRACT

A unique class of chiral additive materials is disclosed for use in cholesteric displays that possess a helical twist power substantially independent of temperature. The additives have a solubility and a helical twist power large enough to be used as a single chiral component with little dilution of the physical properties of the nematic liquid crystal host mixture. The chiral additives may be used in combination with non-chiral additives to provide a helical twisting power substantially independent of temperature suitable for cholesteric displays.

30 Claims, 2 Drawing Sheets

Where R = where UCN is undecyl cyanide:

CHIRAL ADDITIVES FOR CHOLESTERIC DISPLAYS

PRIORITY CLAIM

This application claims the benefit, under 35 U.S.C. §371, of application PCT/US01/14842, filed Jun. 8, 2001, which claims the benefit under 35 U.S.C. §119(e) of application Ser. No. 60/210,485, filed Jun. 9, 2000.

STATEMENT OF GOVERNMENT INTEREST

The invention described herein was made in the performance of work under Contract No. DMI99903655 awarded by the National Science Foundation. Thus, the Government of the United States has certain rights in this invention.

BACKGROUND OF THE INVENTION

1. Field of the Invention

The present invention relates to a unique class of chiral compounds for liquid crystals, and to liquid-crystalline mixtures containing such chiral compounds, and to their use for cholesteric displays and the resulting devices.

2. Description of the Related Art

Cholesteric flat-panel displays are currently under development because of their low power consumption, bright viewing characteristics at wide angles, and high-resolution capability at low cost. Their low-power consumption is a result of the bistable memory characteristic inherent in the technology. As described in the first U.S. patents on this technology (See U.S. Pat. Nos. 5,251,048, 5,384,067, 5,437,811, and 5,453,863), each pixel of the display can exist in a stable color reflective state with any desired reflective intensity or brightness (gray-scale) without any applied power. The degree of brightness is electronically selected by a pulse. A unique feature described in those inventions, is the existence of a threshold in the electronic response to a pulse such that a matrix of pixels can be multiplexed to achieve a high resolution display at low cost without the need of transistor elements (active matrix) at each pixel. Because of the low power and reflective brightness characteristics, cholesteric displays are used in portable or handheld applications where long battery life and versatile viewing capabilities are important.

The reflective properties of cholesteric liquid crystals have been generally known for many years. Sometimes called a chiral nematic, a cholesteric liquid crystal achieves its color reflective property because the molecules are arranged in a helical twist pattern with a periodicity (pitch length) equal to the wavelength of light in the material. The first materials explored with this property were the cholesterol esters. These materials are not only chiral but also liquid crystalline and reflect iridescent colors when the periodicity of the twist corresponds to a reflective wavelength from 400 nm to about 700 nm ["Cholesteric Structure—II: Chemical Significance", p105–119, J. L. Fergason, N. N. Goldberg, R. J. Nadalin, *Liquid Crystals*, Ed. G. H. Brown, G. J. Dienes, M. M. Labes, Gordon and Breach Science Publishers, New York (1966)]. The materials were therefore called cholesteric liquid crystals, a name still used today even though cholesterol materials are seldom used today. Instead, a mixture of chiral and achiral compounds is used as discussed by Gottarelli et al. ["Induced Cholesteric Mesophases: Origin and Application, G. Gottarelli, G. P. Spada, Mol. Cryst. Liq. Cryst., 123, 377–388 (1985)]. Achiral liquid crystalline compounds make up a nematic liquid crystalline host mixture, which has no helical twist by itself. To this host nematic is added a chiral compound to twist up the nematic material into one of a cholesteric structure, hence the name chiral nematic.

The helical arrangement of the molecules provides a self-assembled stack of dielectric layers because of the anisotropy of the refractive index of the molecules. The index of refraction continuously varies along the stack by as much as 0.25 depending upon the nematic material. Because of the helical nature of the refractive index in the layer, the stack will reflect one circular component of a selected bandwidth of colored light. A right handed twisted planar texture will therefore decompose incident unpolarized white light into its right and left components by reflecting the right hand component and transmitting the left. A left-handed twisted material will do the opposite. A left-hand display cell stacked on top of a right-hand cell, both with the same pitch length, will reflect all of the incident light.

According to Bragg's law, the wavelength $\lambda$, of the selective reflection is given by the equation: $\lambda = np$ where p is the pitch of the helical structure and n is the average refractive index of the liquid crystal mixture. In mixtures of a nematic liquid crystal with the chiral additive, the reciprocal of the pitch length is approximately proportional to the concentration X, of the chiral compound, $p^{-1} = \beta_X$ with $\beta$ being the helical twisting power (HTP). Conventional chiral additives available today have twisting powers typically of $\beta < 15\ \mu m^{-1}$ when X is measured in weight percent.

Certain dimethanoldioxolane derivatives have been described in the literature as possessing large HTP values. E.g., "TADDOLs with Unprecedented Helical Twisting Power in Liquid Crystals", H. G. Kuball, B. Weiss, A. K. Beck, D. Seebach, *Helvetica Chimica Acta*, 80, 2507–2514 (1997); "TADDOLs Under Closer Scrutiny—Why Bulky Substituents Make it All Different", A. K. Beck, M. Dobbler, D. A. Plattner, *Helvetica Chimica Acta*, 80, 2073–2083 (1997); and in U.S. Pat. No. 5,637,255. Like other chiral additives, they are also known to generally possess large temperature dependent values of dp/dT and, hence, $d\lambda/dT$. Their temperature dependencies tend to be positive in that the pitch length increases with w increasing temperature, causing a cholesteric material to change from blue to red reflecting. Furthermore, the temperature dependence dp/dT has been shown to depend on the material of the host nematic. See "TADDOLs with Unprecedented Helical Twisting Power in Liquid Crystals", H. G. Kuball, B. Weiss, A. K. Beck, D. Seebach, *Helvetica Chimica Acta*, 80, 2507–2514 (1997).

In order for flat-panel displays to be useful for portable applications, it is necessary for the display be operable over a wide range of temperatures. Outdoor temperatures can range from −20° C. to +50° C. depending on the environment. It would be advantageous if the reflected colors did not change over this temperature range. Implementing this desirable characteristic is not a straightforward task, since nearly all cholesteric liquid crystalline materials are well known to exhibit reflective colors that vary strongly with changes in temperature. Depending on the shape or chemical structure of the chiral molecule, the pitch length p and, hence, the peak reflective wavelength $\lambda$, can increase with temperature (+d$\lambda$/dT) or decrease with temperature (−d$\lambda$/dT). Also, in many cases, $d\lambda/dT$ is not linear over the temperature range of the cholesteric phase.

It should be mentioned at this point that the measurement for the temperature dependence of the pitch is performed using test cells, each of which is 5 $\mu$m thick, and has a hard coat layer on both substrates. There is also an unrubbed polyimide surface on top of the hard coat layers. The measurement for the temperature dependence of the pitch is performed in the following manner. A collimated light is incident on the display at surface normal and the reflected light is detected at 45°. The display is scanned in the wavelength band that includes the peak-reflected wavelength, e.g., 400 nm to 700 nm, or 700 nm to 1500 nm. The cell is switched to the planar texture at each test temperature. The measurement is performed from −20° C. to +70° C. in 10° C. intervals. It should be noted that, for the purposes of a flat temperature dependence, only a portion of the test temperature range, i.e., temperatures between +10° C. to +50° C., are considered. In any event, the maximum change in peak reflected wavelength is then recorded. A mixture is considered to exhibit temperature independent color behavior if the maximum change in the peak reflection wavelength is 30 nm or less across the temperature range of +10° C. to +50° C.

It has been shown that cholesteric displays fabricated using a mixture of two or more chiral compounds as additives can be made to produce a helical twist power and, hence, reflective wavelength that is independent of temperature by combining a chiral compound that has a $+d\lambda/dT$ with one with a $-d\lambda/dT$. U.S. Pat. No. 5,309,265 describes a means of achieving a temperature independent $\lambda$ by combining a plurality of chiral compounds, where both compounds exhibit the same twist sense.

It will be noted that there are a number of factors that preclude employing many previously known chiral compounds in liquid crystals. First of all, a chiral compound must be soluble in the nematic liquid crystal host material; many compounds are simply not soluble or only weakly soluble and, thus, cannot be used. In compounds that are soluble, they may adversely affect the nematic material by substantially reducing the temperature range of the liquid crystalline phase. If the chiral compound has an HTP that is too low, it may be necessary to add a large quantity of the additive which can dilute some of the desirable physical properties of the host nematic needed for the cholesteric display.

Consequently, a need still exists for a chiral additive, which is readily soluble in a nematic host mixture and which can be used individually (i.e., without needing to be combined with other chiral materials) for cholesteric displays that provides a high helical twisting power, substantially independent of temperature in operating ranges suitable for the cholesteric displays. What is also needed is a cholesteric display exhibiting a high helical twisting power, which is substantially independent of temperature in operating ranges suitable for the cholesteric displays, which display includes at least one chiral additive, which is readily soluble in a nematic host mixture. In some cases it would be desirable if the temperature dependence of the cholesteric display could be tailored by the addition of a second additive, e.g., either an achiral compound or a second chiral additive different from the first chiral additive, where the twist senses of the first and second chiral additives are opposite to one another.

SUMMARY OF THE INVENTION

The above and other objectives are fulfilled by the present invention which concerns a unique class of chiral compounds that can be used alone as the optically-active additive or dopant in nematic liquid crystals to achieve a reflective wavelength that is temperature independent or essentially temperature independent, i.e., a $d\lambda/dT$ approaching zero in value, yet without significantly reducing the temperature range of the liquid crystalline phase, or diluting or otherwise adversely affecting its needed physical properties for liquid crystal implementations.

The inventive compounds are derivatives of dioxolanes and have the molecular structure generally indicated in FIG. 1 and reproduced below as general formula I.

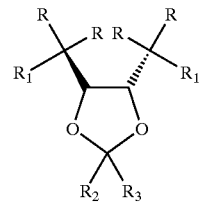

I

The R, $R_1$, $R_2$ and $R_3$ substitutions on the molecule of general formula I control the temperature dependence of the twisting power in the nematic host mixture in a surprisingly superior fashion. Generally, the $R_2$ and $R_3$ groups at the number 2 position of the dioxolane ring independently are hydrogen, methyl or another lower alkyl group, or a substituted aryl or biaryl unit, while the $R_1$ groups independently each are a hydroxyl, alkoxy, aryloxy, or arylalkoxy group. The R groups in general formula I indicate a group of general formula II, which is as follows:

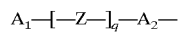

II where $A_1$ is an aromatic group, an acyclic aliphatic group, or an alicyclic group (e.g., a mono- or polycyclic aryl group, a straight chain or branched chain alkyl group, an arylalkyl group, an arylalkenyl group, a cycloalkyl group, a cycloalkenyl group), and $A_1$ can be a substituted or unsubstituted group. For example, $A_1$ can be benzyl, cinnamyl, phenethyl, cyclohexyl, and the like. Z is a group selected from —O—, —OCO—, or —S—, and the coefficient q is 0 or 1. Z can also be $(CH_2)_nO$ with the coefficient n being 0 to 5 and the coefficient q being 1. $A_2$ is a bivalent radical of naphthalene that may additionally be substituted. Preferably, $A_2$ is a bivalent radical (2,6- or 1,5-disubstituted) of naphthalene, which may be unsubstituted or substituted (e.g., methyl, cyano, halogeno, amino, nitro, or hydroxyl substituents). The ring structure of $A_2$, or $A_1$ if it is cyclic, optionally can be heterocyclic, such as by replacement of one or more CH member(s) of the ring structure with N, O and/or S (e.g., a bivalent radical of quinoline, xanthene, carbazole, or acridine).

In one preferred embodiment, each R substituent of general formula I is independently selected as:

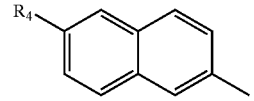

where $R_4$ can be represented by general formula III as follows:

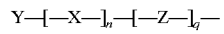

III where n is an integer value of 0 or 1 or more, X is —CH═CH—CH$_2$—, or —(CH$_2$)$_m$— where m is an integer value of 1, 2, 3, or more. Y is a radical of an aromatic hydrocarbon, an acyclic aliphatic hydrocarbon, or an alicyclic hydrocarbon group (e.g., a mono- or polycyclic aryl group, a straight chain or branched chain alkyl group, a cycloalkyl group, a cycloalkenyl group, and the like), and Y can be a substituted or unsubstituted group. Z and q have the same respective meanings as defined above relative to general formula II.

In one preferred embodiment, $R_4$ is an aryloxy, an arylalkoxy, an arylalkyleneoxy, or an arylalkenyleneoxy group. Examples of $R_4$ advantageously may include, for instance, benzyloxy ($C_6H_5$—$CH_2$—O—), cinnamyloxy ($C_6H_5$—CH=CH—$CH_2$—O—), phenethyloxy ($C_6H_5$—$CH_2$—$CH_2$—O—), and the like, where $R_1$ is a hydroxy group and $R_2$ and $R_3$ are methyl groups.

Additionally, the specific structures of the four R groups present in formula I or FIG. 1 can be identical to each other or they can independently vary from each other within the guidelines indicated above and herein.

The inventive optically-active, chiral additives according to the formula of FIG. 1 contain a sufficiently high helical twisting power (HTP) so that only a relatively small amount of the chiral additive is required to twist the nematic phase to a pitch length where it reflects wavelengths in the visible or infrared portion of the electromagnetic spectrum. On the other hand, the HTP of the additive is not inordinately high either, so that the invention can avoid undesired gradients in concentration, which could cause undesired inhomogeneities in the display. The present invention thereby avoids the need to combine separate types of chiral compounds in order to achieve a very high degree of temperature independence. While the present invention does not necessarily exclude the possibility, and in fact does contemplate, use of mixtures of different inventive chiral compounds within the scope of the formula of FIG. 1, the important point is that the inventive chiral compounds can be effectively used singly in a liquid-crystalline nematic mixture deployed in a light modulating apparatus to avoid the need for chiral additive combinations.

DETAILED DESCRIPTION OF THE INVENTION

Figure 1:
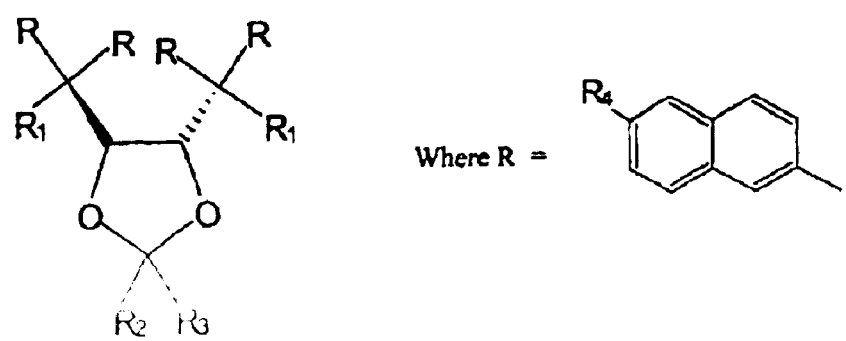
FIG. 1 is the general chemical structure of the dioxolane derivatives according to the present invention, where the $R_1$, $R_2$ $R_3$, and $R_4$ substituents control the temperature dependence of the twisting power in a superior manner.

In this invention, a new class of derivatives of dioxolanes embodied by the formula of FIG. 1 has been discovered that provide a substantially temperature independent dp/dT over a wide operating temperature range when added to nematic liquid crystalline mixtures with physical properties that are useful in cholesteric displays, including commercially viable cholesteric displays. The inventive chiral compounds are especially useful as additives to nematic liquid crystals for use in cholesteric displays to achieve needed properties for their practical use, particularly in portable device applications. Significantly, this invention provides this utility while only requiring the use of a single type of chiral additive compound within the scope of the invention, as described herein, and without requiring a mixture of different types of chiral additives.

Commercially viable displays require a liquid crystal mixture that has a dielectric anisotropy, birefringence and desired elastic and viscosity coefficients to provide a display with suitable brightness, contrast, and speed. The dielectric anisotropy and viscosity must be such that low voltage pulses can be used to reduce the cost of the electronic drive chips as well as implement drive schemes and waveforms for rapidly addressing the display. The birefringence has to be large to provide high brightness. Furthermore, the materials must not provide undesirable features to the display such as image sticking or phase separation. Cholesteric displays therefore require very special cholesteric materials. Cholesteric displays incorporating the inventive dioxolane derivatives satisfactorily meet all these criteria and requirements, while providing superior temperature independence performance and so forth.

Namely, the invention provides chiral compound additives to nematic liquid crystals that provide at least the following features important for cholesteric displays:

1. Solubility in nematic liquid crystals that have the physical properties necessary for cholesteric displays.
2. Possess a helical twist power (HTP) generally ranging from 15 $\mu m^{-1}$ to 200 $\mu m^{-1}$, and more usually from 30 $\mu m^{-1}$ to 90 $\mu m^{-1}$. HTP values in this range are not so small as to dilute the important physical properties of nematic liquid crystals when twisted to reflect light in the visible spectrum. In addition, these values are not so large that slight inhomogeneities in the mixture caused by phase separation can disfigure the display.
3. Provide a substantially temperature independent HTP in the cholesteric phase over the operating temperature range of cholesteric displays of commercial value.
4. Do not decompose under ultraviolet light of exposures under common environmental conditions.
5. Do not chemically react with the host nematic liquid crystal.
6. Possess the property that the temperature dependence can be modified by the addition of an achiral additive to the nematic liquid crystal. Such an additive may or may not posses a liquid crystalline phase.

As compared to the competing contemporarily available chiral additives that have twisting powers typically of β<15 $\mu m^{-1}$ when X is measured in weight percent, the new soluble chiral additive materials, invented here, have values of β approaching 80 $\mu m^{-1}$. This is a substantial improvement since the concentration of the chiral additive in this invention can be so small as to have a near negligible effect on the physical properties of the nematic liquid crystal.

Chiral nematic liquid crystalline materials within the scope of this invention, which include an inventive chiral additive and a nematic host mixture, can be implemented in cholesteric liquid crystal displays, electro-optical cells, and light modulating apparatuses in manners, arrangements and/or systems consistent with the descriptions, such as set forth in U.S. Pat. Nos. 5,251,048, 5,384,067, 5,437,811, and 5,453,863, whose descriptions are incorporated by reference.

EXAMPLES

Figure 2:
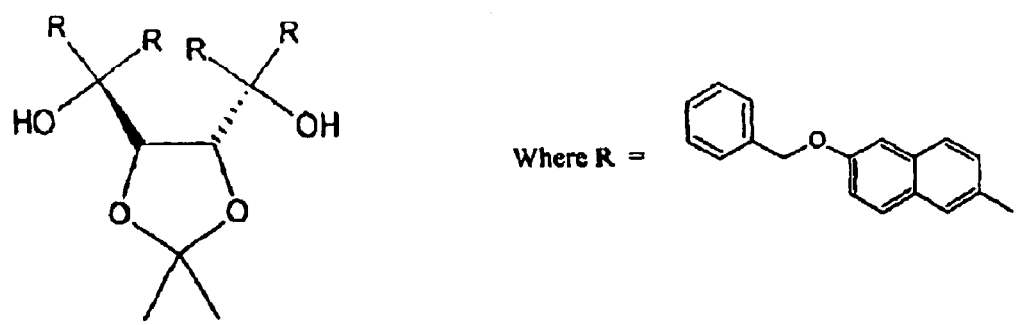
FIG. 2 is the chemical structure of a preferred inventive compound embodied by the formula of FIG. 1, viz., (4R, 5R)-2,2-dimethyl-α,α,α',α'-tetrakis[6-(benzyloxy)naphth-2-yl]-1,3-dioxolane-4,5-dimethanol, which has been experimentally demonstrated to provide low dλ/dT in certain nematic host mixtures.

Synthesis Scheme for Chiral Additive:

One illustrative inventive compound, (4R,5R)-2,2-dimethyl-α,α,α',α'-tetrakis[6-(benzyloxy)naphth-2-yl]-1,3-dioxolane-4,5-dimethanol, is shown in FIG. 2 and is reproduced below. The dimethanoldioxolane has 2,6-substituted naphthalene units.

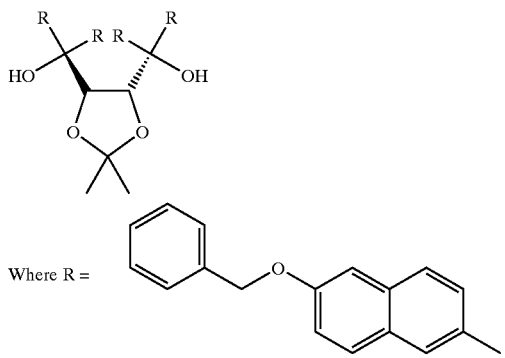

The inventive compound of FIG. 2 was synthesized according to the following protocol with reference to the reaction Scheme I provided below.

Synthesis of 2-(Benzyloxy)-6-bromonaphthalene (2) Intermediate:

A mechanically stirred mixture of 6-bromonaphth-2-ol (10.00 g, 0.04483 mol), benzyl bromide (6.97 g, 0.0408 mol), potassium carbonate (11.26 g, 0.08147 mol) and butan-2-one (350 ml) was heated under reflux for 24 hrs. (GLC and TLC analyses revealed a complete reaction). The potassium carbonate was filtered off and the filtrate was washed with water before being dried ($MgSO_4$). The drying agent was filtered off and the solvent was removed in vacuo to give a pale orange solid. The crude product was crystallized twice from ethanol and was dried in vacuo ($P_2O_5$, $CaCl_2$, paraffin wax, 48 h) to afford white crystals.
Yield=11.97 g (94%), mp 113–114° C.

Synthesis of Product Compound—Compound (4):
(4R,5R)-2,2-dimethyl-α,α,α',α'-tetrakis[6-(benzyloxy)naphth-2-yl]-1,3-dioxolan-4,5-dimethanol (4):

n-Butyllithium (5.37 ml, 2.5M in hexane, 0.0134 mol) was added dropwise at −74° C. to −77° C. to a mechanically stirred, cooled (−77° C.) solution of compound 2 (4.20 g, 0.0134 mol) in dry tetrahydrofuran (350 ml) under dry argon. Once the addition was complete, the reaction mixture was maintained under these conditions for a further 2 hrs. (GLC analysis revealed a complete reaction) before the reaction mixture was allowed to warm to −25° C.

2,3-O-Isopropylidene-L-tartrate (0.73 g, 0.03345 mol) was added to the reaction mixture at −20° C. to −25° C. (exothermic) and the reaction mixture was allowed to warm to room temperature. The reaction mixture was stirred at room temperature for a further 15 hrs. before saturated ammonium chloride (60 ml) was added and the mixture stirred for a further 4 hrs. The reaction mixture was washed with diethyl ether (3×75 ml) and the combined organic washings were dried ($MgSO_4$). The drying agent was filtered off and the solvent was removed in vacuo to give an orange semi-solid.

The crude product was purified twice by column chromatography [silica gel/hexane, ethyl acetate, 4:1] followed by further chromatography [silica gel/hexane, diethyl ether, 4:1]. The product was crystallized from toluene to afford a pale yellow solid, which was dried in vacuo ($P_2O_5$, $CaCl_2$, paraffin wax, 48 h).

Yield=7.30 g (50%).

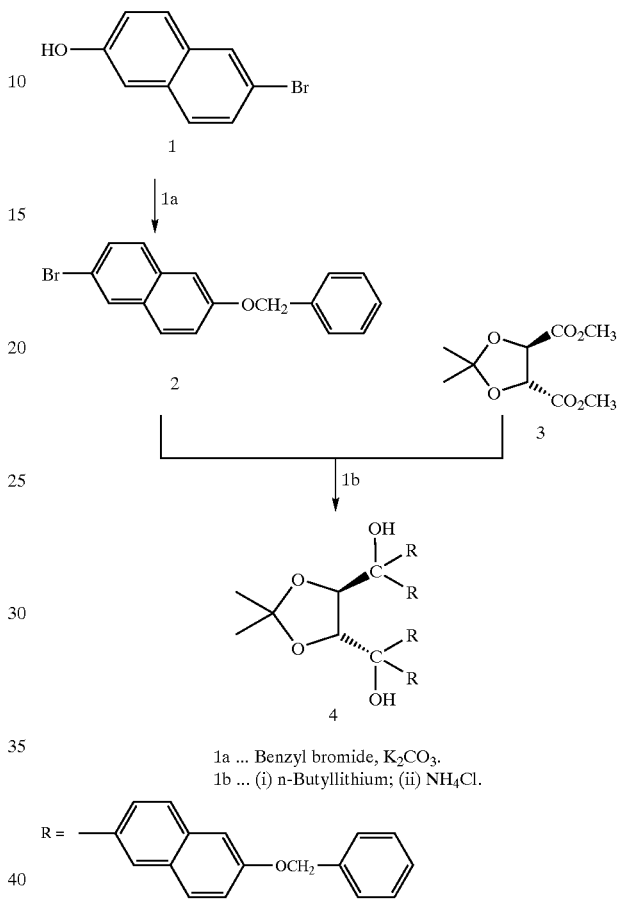

Scheme 1

1a ... Benzyl bromide, $K_2CO_3$.
1b ... (i) n-Butyllithium; (ii) $NH_4Cl$.

Example 1

Figure 3:
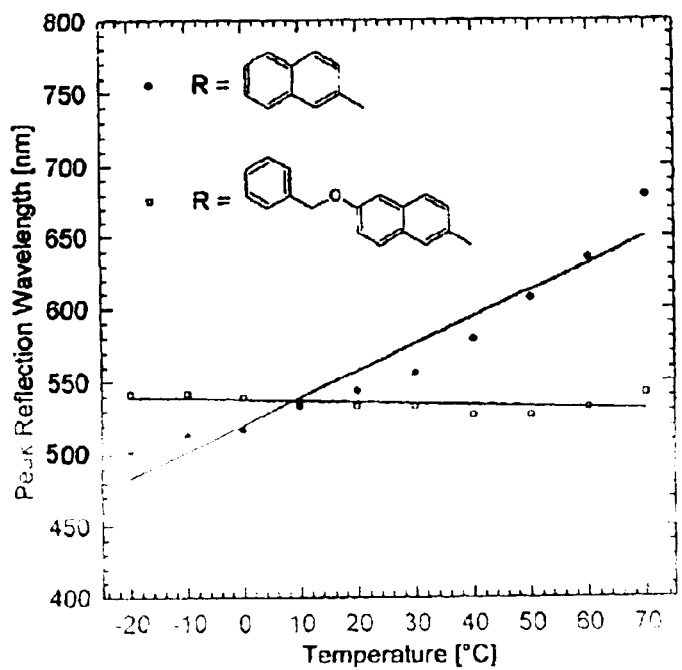
FIG. 3 is a graph showing the peak reflection wavelength (nm) versus temperature results for experimental tests performed with respect to a variation in color for two compounds in the E44 nematic host mixture. A substitution on the naphthalene units shows a dramatic change in the dλ/dT results.

Experimental studies were performed on the dimethanoldioxolane compound (4) described above and of the structure shown in FIG. 2, and separately on (4R,5R)-2,2-dimethyl-α,α,α',α'-tetrakis[naphth-2-yl]-1,3-dioxolane-4,5-dimethanol as a comparative compound, each in a E44 nematic host mixture, the results of which were plotted in FIG. 3 as a graph showing the peak reflection wavelength (nm) versus temperature. The respective cholesteric liquid crystal mixtures prepared for conducting these experimental studies were as follows.

| Component | Component amt. (wt %) |
|---|---|
| COMPOSITION 1 formulation: | |
| 2-naphthyl as the R groups on the dimethanol-dioxolane (comparative compound) | 3.4% |
| E44 | 96.6% |

-continued

| Component | Component amt. (wt %) |
|---|---|
| COMPOSITION 2 formulation: | |
| 6-benzyloxynaphth-2-yl as the R groups on the dimethanoldioxolane (compound (4), FIG. 2 compound) | 10.0% |
| E44 | 90.0% |

It will be noted that E44 is commercially available nematic liquid crystal mixture that was obtained from Merck KgaA in Darmstadt, Germany through EM Industries in Hawthorne, N.Y. It will also be noted that the percentage of compound (4), and thus the percentage of E44, advantageously can be varied to achieve the desired reflective wavelength. For example, varying the percentage of compound (4) from 10 wt % to 2 wt % changes the reflective wavelength from the visible into the infrared. Finally, it will be noted that other additive materials can be included in the cell material to improve other cell properties.

As to the cholesteric display test cell arrangement used, both mixtures, i.e., Compositions 1 and 2, were vacuum filled in separate surface stabilized cholesteric displays with a 5 μm cell spacing. To accomplish this, two glass plate substrates were put together using an epoxy material around the perimeters with the substrates separated by 5 micron spacers and a small hole left in the perimeter seal for introducing the liquid crystal. The inner faces of the glass substrates were coated with indium-tin oxide (ITO), a standard insulating layer, and a polyimide layer for liquid crystal alignment. The back plate was painted black. The liquid crystal mixture was vacuum filled into the provided cell so that each liquid crystal mixture was sandwiched between the two glass plate substrates.

The arrangement used to control the temperature of the liquid crystal mixtures samples being tested was as follows. A liquid nitrogen cryostat was used to control temperature on the test cells. The cryostat had a cold finger and a heater. The cryostat system fin was obtained from Janis Cryogenics. A white light source was used with a monochromator, both obtained from Oriel. A silicon detector was used to detect the light intensity. To measure the color, the cell was switched to the reflecting planar state at each temperature and the peak reflection wavelength was determined. The peak reflection wavelength of the cells was measured with incident light at the surface normal and reflected light detected at 45°. The switching pulse used had a magnitude (amplitude and width) high enough to transform the texture to the reflecting planar texture at each temperature. The pulse was an AC square pulse. Data points were typically acquired every 10° C. from −20° C. to about +70° C. The results of these measurements are plotted in FIG. 3.

The compound of FIG. 2 was found through these experimental studies to possess a substantially temperature independent HTP in the nematic mixture E44, which is suitable for cholesteric displays. The HTP for this compound at room temperature in E44 is 31 $\mu m^{-1}$. The HTP for the base compound (unsubstituted naphthalene units) is 91 $\mu m^{-1}$. A plot of the temperature dependence of the compound according to the present invention, a compound containing (4R,5R)-2,2-dimethyl-α,α,α',α'-tetrakis[6-(benzyloxy)naphth-2-yl]-1,3-dioxolan-4,5-dimethanol, versus that of the comparative reference compound, i.e., a similar compound containing a small amount by weight of (4R,5R)-2,2-dimethyl-α,α,α',α'-tetrakis[naphth-2-yl]-1,3-dioxolane-4,5-dimethanol, which is strongly temperature dependent, is shown in FIG. 3. It should be noted that both molecules exhibit a linear temperature dependence from −20° C. to +70° C.

In addition to the use of a single chiral additive, independence of the helical twisting power with temperature advantageously can be obtained by mixing two dioxolane materials that are structurally different and that exhibit opposite twist senses.

Example 2
Additional Studies Involving Achiral Compound Additive:

The change in color of a liquid crystal mixture containing a chiral compound (viz., compound 4, FIG. 2 compound) and a host mixture (viz. E44) along with a small amount of an achiral non-liquid crystalline compound (undecyl cyanide at 4% by weight) was investigated. The components were mixed according to the following proportions as Composition 3:

| Component | Component amt. (wt %) |
|---|---|
| COMPOSITION 3 formulation: | |
| 6-benzyloxynaphth-2-yl as the R groups on the dimethanoldioxolane (compound (4), FIG. 2 compound) | 11.0% |
| E44 | 85.0% |
| UCN (undecyl cyanide, $C_{11}H_{23}CN$) | 4.0% |

Figure 4:
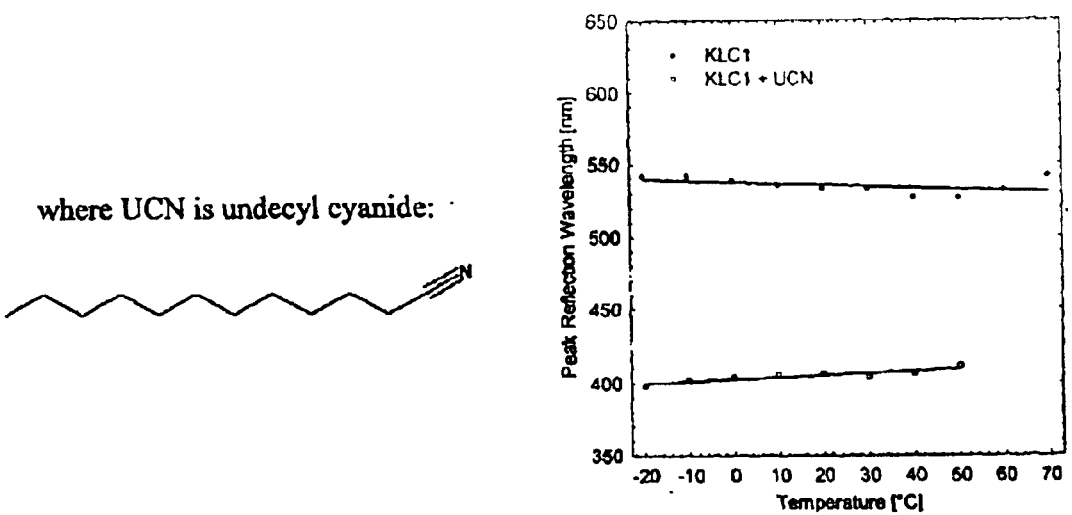
FIG. 4 is a graph showing the peak reflection wavelength (nm) versus temperature results for experimental tests performed on the dimethanoldioxolane compound from FIG. 2 in E44 nematic host mixture tested with and without UCN additive.

The resulting liquid-crystalline mixture containing the achiral additive was filled into a cell and tested using the arrangement described in Example 1. The results of these additional experiments investigating the possible effect of certain achiral additives to the liquid crystalline nematic mixture are shown in FIG. 4, and the plot of the results obtained for Composition 2 in Example 1 as indicated in FIG. 3 was included for sake of comparison. The inventive chiral dimethanoldioxolane compound used for these studies was used to twist the nematic phase to a blue reflecting pitch length. Referring to FIG. 4, a subtle difference between the two curves was clearly evident. Without the achiral additive, the $d\lambda/dT$ is nearly flat with a slightly negative value, whereas with the achiral additive, the $d\lambda/dT$ is nearly flat with a slightly positive value. The helical twisting power for the dimethanoldioxolane compound is similar for the two nematic mixtures in FIG. 4 with the additive host mixture showing a slightly higher HTP.

It should be noted that UCN is representative of a class of achiral compounds of the general structure $R^1CN$ where $R^1$=alkyl. $R^1$=$C_{11}H_{23}$— for UCN itself.

Thus, a further discovery of this invention is that fine-tuning can therefore be performed using certain achiral non-liquid crystalline compounds added to a cholesteric system with a nematic host mixture and a single chiral compound.

For practicing this further embodiment, the achiral additive, namely, aliphatic nitrites, can be commercially obtained from Aldrich Chemicals or prepared by conventionally known methods. Useful alkyl nitrites as the achiral additive include 5C-17C alkanenitriles, and more preferably 8C-14C straight chain or n-alkane nitrites. One preferred alkyl nitrile is undecanenitrile, using IUPAC nomenclature (alternatively, referred to as undecyl cyanide, in common nomenclature). These achiral additives have been found to be effective in amounts of approximately 2 to 6 wt % of the overall liquid-crystalline mixture.

Although E44 was exemplified above, virtually any nematic host mixture, including cyanobiphenyls known in the art, can be used in the practice of this invention. The inventive chiral compounds are readily soluble, as required, in many commercially available nematic host mixtures.

While this invention has been described in terms of its preferred embodiments, those skilled in the art will recognize that the invention can be practiced with modification within the spirit and scope of the appended claims.

APPENDIX: REFERENCES CITED

1. U.S. Pat. No. 5,251,048: "Method and Apparatus of Electronic Switching of a Reflective Color Display", J. W. Doane, D. -K. Yang, October 1993.
2. U.S. Pat. No. 5,384,067: "Grey Scale Liquid Crystal Material", J. W. Doane, D. -K. Yang, January 1995.
3. U.S. Pat. No. 5,437,811: "Liquid Crystalline Light Modulating Device and Material", J. W. Doane, D. -K. Yang, L. -C. Chien, August 1995.
4. U.S. Pat. No. 5,453,863: "Multistable Chiral Nematic Displays", J. West, D. -K. Yang, September 1995.
5. "Cholesteric Structure—II: Chemical Significance", p105–119, J. L. Fergason, N. N. Goldberg, R. J. Nadalin, *Liquid Crystals*, Ed. G. H. Brown, G. J. Dienes, M. M. Labes, Gordon and Breach Science Publishers, New York (1966).
6. "Induced Cholesteric Mesophases: Origin and Application, G. Gottarelli, G. P. Spada, Mol. Cryst. Liq. Cryst., 123, 377–388 (1985).
7. U.S. Pat. No. 5,309,265: "Short Pitch LC layer with a temperature Independent $\lambda_0$ and Containing a Nematic LC Doped with Plural Chiral Additives Having the Same Twist Sense", R. Buchecker, J. Funfschilling, M. Schadt, May 1994.
8. "TADDOLs with Unprecedented Helical Twisting Power in Liquid Crystals", H. -G. Kuball, B. Weiss, A. K. Beck, D. Seebach, *Helvetica Chimica Acta*, 80, 2507–2514 (1997).
9. "TADDOLs Under Closer Scrutiny—Why Bulky Substituents Make it All Different", A. K. Beck, M. Dobbler, D. A. Plattner, *Helvetica Chimica Acta*, 80, 2073–2083 (1997).
10. U.S. Pat. No. 5,637,255: "Chiral Dioxolanes", S. Kelly, M. Schadt, June 1997.

What is claimed is:

1. An optically active compound of the formula:

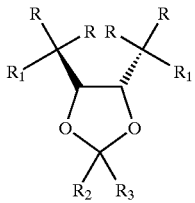

where the $R_2$ and $R_3$ groups are a lower alkyl group or an aryl or biaryl unit while the $R_1$ groups independently each are a hydroxyl, alkoxyl, aryloxy, or arylalkoxy group, the R groups each represent a group as follows:

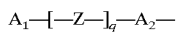

where $A_1$ is an aromatic group, an acyclic aliphatic group, or an alicyclic group, and $A_1$ can be a substituted or unsubstituted, Z is a group selected from —O—, —OCO—, or —S—, and the coefficient q is 0 or 1 or Z is $(CH_2)_nO$ where the coefficient n is 0 to 5 and the coefficient q is 1, and $A_2$ is a bivalent radical of a naphthalene group, and the cyclic structure of $A_2$, or $A_1$ if it is cyclic, can be heterocyclic.

2. The optically active compound of claim 1, where each R substituent is independently selected as:

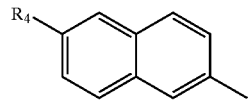

where $R_4$ represents a group as follows:

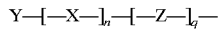

where n is an integer value of $\geq 0$, X is —CH=CH—CH$_2$—, or $(CH_2)_m$— where m is an integer value of $\geq 1$, Y is a radical of an aromatic hydrocarbon, an acyclic aliphatic hydrocarbon, or an alicyclic hydrocarbon, and Y can be substituted or unsubstituted.

3. The optically active compound of claim 2, where $R_4$ is an aryloxy radical, an arylalkoxy radical, an arylalkyleneoxy, or an arylalkenyleneoxy radical.

4. (4R,5R)-2,2-dimethyl-α,α,α',α'-tetrakis[6-(benzyloxy) naphth-2-yl]-1,3-dioxolane-4,5-dimethanol.

5. A liquid crystalline mixture, comprising:
   a liquid-crystalline base having liquid crystalline properties;
   at least one optically active compound of the formula:

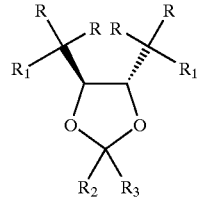

where $R_2$ and $R_3$ are a lower alkyl group or an aryl or biaryl unit while the $R_1$ groups independently each are a hydroxyl, alkoxyl, aryloxy, or arylalkoxy group, the R groups each represent a group as follows:

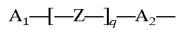

where $A_1$ is an aromatic group, an acyclic aliphatic group, or an alicyclic group, and $A_1$ can be-o substituted or unsubstituted, Z is a group selected from —O—, —OCO—, or —S—, and the coefficient q is 0 or 1, or Z is $(CH_2)_nO$ where the coefficient n is 0 to 5 and the coefficient q is 1 and $A_2$ is a bivalent radical of a naphthalene group, and the cyclic structure of $A_2$, or $A_1$ if it is cyclic, can be heterocyclic.

6. The liquid crystalline mixture of claim 5, where each R substituent is independently selected as:

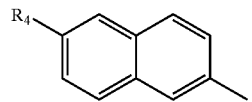

where $R_4$ represents a group as follows:

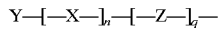

where n is an integer value of $\geq 0$, X is —CH=CH—CH$_2$, or —$(CH_2)_m$— where m is an integer value of $\geq 1$, Y is a radical of an aromatic hydrocarbon, an acyclic aliphatic hydrocarbon, or an alicyclic hydrocarbon, and Y can be substituted or unsubstituted.

7. The liquid crystalline mixture of claim 6, where $R_4$ is an aryloxy radical, an arylalkoxy radical, an arylalkyleneoxy, or an arylalkenyleneoxy radical.

8. The liquid crystalline mixture of claim 5, further including an achiral non-liquid crystalline compound.

9. The liquid crystalline mixture of claim 8, wherein the achiral non-liquid crystalline compound comprises $R^1$—C≡N, where $R^1$ represents an aliphatic group.

10. The liquid crystalline mixture of claim 9, wherein $R^1$—C≡N represents an alkylnitrile.

11. The liquid crystalline mixture of claim 9, wherein $R^1$—C≡N represents undecanenitrile.

12. A liquid crystalline mixture, comprising:
a liquid-crystalline base having liquid crystalline properties;
at least one optically active compound of the formula (4R,5R)-2,2-dimethyl-α,α,α',α'-tetrakis[6-(benzyloxy) naphth-2-yl]-1,3-dioxolane-4,5-dimethanol.

13. The liquid crystalline mix of claim 12, further including an achiral non-liquid crystalline compound.

14. The liquid crystalline mixture of claim 13, wherein the achiral non-liquid crystalline compound comprises $R^1$—C≡N, where $R^1$ represents an aliphatic group.

15. The liquid crystalline mixture of claim 14, wherein $R^1$—C≡N represents an alkylnitrile.

16. The liquid crystalline mixture of claim 14, wherein $R^1$—C≡N represents undecanenitrile.

17. An electro-optical cell comprising a layer including a liquid crystalline mixture sandwiched between two substrate means, and means for applying an electric potential to the substrate means, wherein the liquid crystalline mixture comprises:
a liquid-crystalline base having liquid crystalline properties;
at least one optically active compound of the formula:

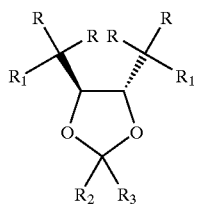

where the $R_2$ and $R_3$ groups are a lower alkyl group or an aryl or biaryl unit while the $R_1$ groups independently each are a hydroxyl, alkoxyl, aryloxy, or arylalkoxy group, the R groups each represent a group as follows:

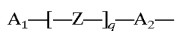

where $A_1$ is an aromatic group, an acyclic aliphatic group, or an alicyclic group, and $A_1$ can be-a substituted or unsubstituted, Z is a group selected from —O—, —OCO—, or —S—, and the coefficient q is 0 or 1 or Z is $(CH_2)_nO$ where the coefficient n is 0 to 5 and the coefficient q is 1 and $A_2$ is a bivalent radical of a naphthalene group, and the cyclic structure of $A_2$, or $A_1$ if it is cyclic, can be heterocyclic.

18. A light modulating apparatus comprising said electro-optical cell of claim 17.

19. The light modulating apparatus of claim 18, wherein the light modulating apparatus comprises a cholesteric display.

20. A electro-optical cell comprising a layer including a liquid crystalline mixture sandwiched between two substrate means, and means for applying an electric potential to the substrate means, wherein the liquid crystalline mixture, comprises:
a liquid-crystalline base having liquid crystalline properties;
at least one optically active compound of the formula (4R,5R)-2,2-dimethyl-α,α,α',α'-tetrakis[6-(benzyloxy) naphth-2-yl]-1,3-dioxolane-4,5-dimethanol.

21. A light modulating apparatus comprising said electro-optical cell of claim 20.

22. The light modulating apparatus according to claim 21, wherein the light modulating apparatus comprises a cholesteric display.

23. An electro-optical cell comprising:
a layer comprising:
at least 70 weight percent (wt %) nematic host mixture; and
at least about 2 wt % (4R,5R)-2,2-dimethyl-α,α,α',α'-tetrakis[6-(benzyloxy)naphth-2-yl]-1,3-dioxolane-4, 5-dimethanol;
first and second substrates disposed above and below, respectively, the layer, and
first and second conductors physically coupled to the first and second substrates, respectively, which permit an electrical potential to be applied across the layer.

24. The electro-optical cell of claim 23, wherein the layer further comprises about 2–6 wt % achiral material.

25. The electro-optical cell of claim 23, wherein the layer further comprises a chiral material different from (4R,5R)-2,2-dimethyl-α,α,α',α'-tetrakis[6-(benzyloxy)naphth-2-yl]-1,3-dioxolane-4,5-dimethanol and having an opposite twist sense.

26. A light modulating apparatus comprising said electro-optical cell of claim 23.

27. The light modulating apparatus of claim 26, wherein the light-modulating apparatus comprises a cholesteric display having a temperature independent reflective wavelength.

28. The optically active compound of claim 1, where each R substituent is independently selected as:

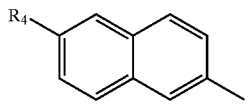

where $R_4$ is an aryloxy radical, an arylalkoxy radical, an arylalkyleneoxy, or an arylalkenyleneoxy radical.

29. The liquid crystalline mixture of claim 5, where each R substituent is independently selected as:

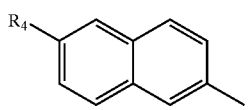

where $R_4$ is an aryloxy radical, an arylalkoxy radical, an arylalkyleneoxy, or an arylalkenyleneoxy radical.

30. The electro-optical cell of claim 17, where each R substituent is independently selected as:

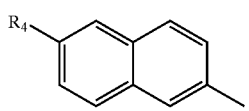

where $R_4$ is an aryloxy radical, an arylalkoxy radical, an arylalkyleneoxy, or an arylalkenyleneoxy radical.

* * * * *

UNITED STATES PATENT AND TRADEMARK OFFICE
CERTIFICATE OF CORRECTION

PATENT NO. : 6,830,789 B2
DATED : December 14, 2004
INVENTOR(S) : Joseph W. Doane et al.

It is certified that error appears in the above-identified patent and that said Letters Patent is hereby corrected as shown below:

Column 12,
Line 42, after "be" delete "- o".

Column 13,
Line 47, after "be" delete "- a".

Signed and Sealed this

Twenty-second Day of March, 2005

JON W. DUDAS
*Director of the United States Patent and Trademark Office*

UNITED STATES PATENT AND TRADEMARK OFFICE
CERTIFICATE OF CORRECTION

PATENT NO. : 6,830,789 B2
APPLICATION NO. : 09/937210
DATED : December 14, 2004
INVENTOR(S) : Joseph W. Doane et al.

It is certified that error appears in the above-identified patent and that said Letters Patent is hereby corrected as shown below:

Title Page, Item (75) Inventors should read: Joseph W. Doane, Kent, OH (US); Asad A. Khan, Kent, OH (US); Alexander J. Seed, Stow, OH (US); Olusegun M. Falana, Fulshear, TX (US)

Signed and Sealed this
Twenty-first Day of April, 2015

Michelle K. Lee
*Director of the United States Patent and Trademark Office*